(12) United States Patent
Gautieri et al.

(10) Patent No.: US 11,649,440 B2
(45) Date of Patent: May 16, 2023

(54) THERMOSTABILIZED AMADORIASES AND USES THEREOF

(71) Applicants: FONDAZIONE ISTITUTO ITALIANO DI TECNOLOGIA, Genoa (IT); POLITECNICO DI MILANO, Milan (IT)

(72) Inventors: Alfonso Gautieri, Milan (IT); Emilio Parisini, Milan (IT); Federica Rigoldi, Milan (IT); Stefano Donini, Milan (IT); Alberto Redaelli, Milan (IT)

(73) Assignees: FONDAZIONE ISTITUTO ITALIANO DI TECNOLOGIA, Genoa (IT); POLITECNICO DI MILANO, Milan (IT)

( * ) Notice: Subject to any disclaimer, the term of this patent is extended or adjusted under 35 U.S.C. 154(b) by 289 days.

(21) Appl. No.: 16/623,241

(22) PCT Filed: Jun. 21, 2018

(86) PCT No.: PCT/IB2018/054582
§ 371 (c)(1),
(2) Date: Dec. 16, 2019

(87) PCT Pub. No.: WO2018/235031
PCT Pub. Date: Dec. 27, 2018

(65) Prior Publication Data
US 2021/0189353 A1    Jun. 24, 2021

(30) Foreign Application Priority Data
Jun. 23, 2017 (IT) .......................... 102017000070452

(51) Int. Cl.
*C12N 9/06* (2006.01)
*G01N 33/50* (2006.01)

(52) U.S. Cl.
CPC ....... *C12N 9/0022* (2013.01); *G01N 33/5091* (2013.01); *G01N 2333/906* (2013.01); *G01N 2800/042* (2013.01)

(58) Field of Classification Search
CPC .................................................. G01N 33/5091
See application file for complete search history.

(56) References Cited

FOREIGN PATENT DOCUMENTS

| EP | 1344828 A1 | 9/2003 |
| WO | 2008013874 A1 | 1/2008 |
| WO | 2009140343 A1 | 11/2009 |

OTHER PUBLICATIONS

Database UniProt Jun. 7, 2017.
Kim S. et al., "Cumulative effect of amino acid substitution for the development of fructosyl valine-specific fructosyl amine oxidase",Enzyme and Microbial Technology, vol. 44, No. 1, Jan. 6, 2009, pp. 52-56.
Kim Seunsu et al., "Engineering of dye-mediated dehydrogenase property of fructosyl amino acid oxidases by site-directed mutagenesis studies of its putative proton relay system", Biotechnology Letters, vol. 32, No. 8, Mar. 11, 2010, pp. 1123-1129.
Rigoldi F. et al., "Molecular dynamics simulations provide insights into the substrate specificity of FAOX family members", Jul. 19, 2016 Molecular Biosystems, Jul. 19, 2016, vol. 12, N. 8, pp. 2622-2633.
Rigoldi F. et al., "Thermal stabilization of the deglycating enzyme Amadoriase I by rational design", Scientific Reports,vol. 8, No. 1, 3042, Feb. 14, 2018.
Sakaue Ryoichi et al., "Thermostabilization of bacterial fructosyl-amino acid oxidase by directed evolution" Applied and Environmental Microbiology, vol. 69, No. 1, Jan. 1, 2003, pp. 139-145.
Search Report and Written Opinion of Italian Application No. IT 2017000070452 dated Jan. 25, 2018.
Search Report and Written Opinion of PCT/IB2018/054582 dated Sep. 21, 2018.

*Primary Examiner* — Bin Shen
(74) *Attorney, Agent, or Firm* — Silvia Salvadori, P.C.; Silvia Salvadori

(57) ABSTRACT

The present invention refers to Amadoriase enzyme protein variants having de-glycating activity and improved thermostability compared to the wild type Amadoriase. The present invention refers also to the use of the thermostabilized Amadoriase as deglycating agent, preferably in the food industry. Moreover, the present invention refers to the use of the thermostabilized Amadoriase as diagnostic and/or therapeutic tools. Preferably, the Amadoriase enzyme protein variants of the invention can be used for determining the level of glycated haemoglobin in a biological sample and therefore for monitoring diabetes.

9 Claims, 2 Drawing Sheets

Figure 1:
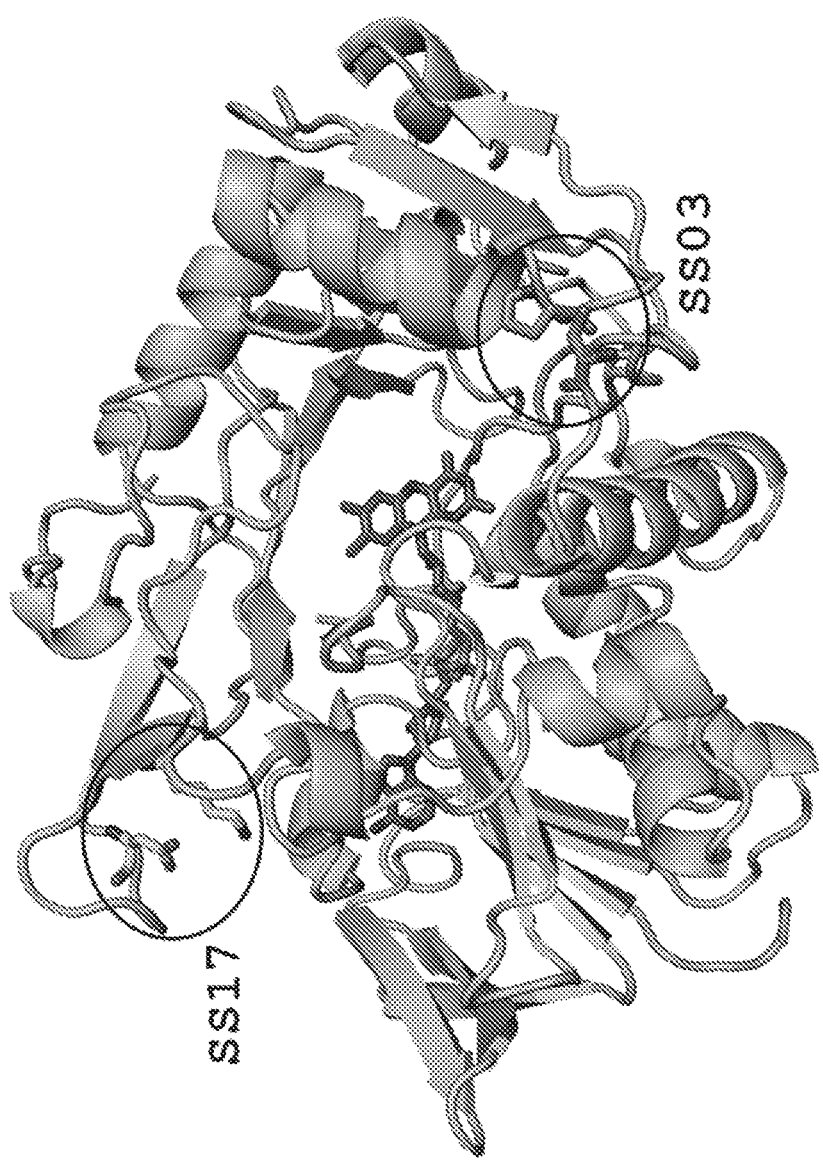

Specification includes a Sequence Listing.

SEQUENCE LISTING

```
<160> NUMBER OF SEQ ID NOS: 7

<210> SEQ ID NO 1
<211> LENGTH: 445
<212> TYPE: PRT
<213> ORGANISM: Artificial Sequence
<220> FEATURE:
<223> OTHER INFORMATION: Amino acid Sequence Wild Type Amadoriase I

<400> SEQUENCE: 1

Met Ala Pro Ser Ile Leu Ser Thr Glu Ser Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270
```

```
Pro Asp Glu Asp Lys His Glu Leu Lys Ile Cys Asp Glu His Pro Gly
            275                 280                 285
Tyr Cys Asn Phe Leu Pro Asp Pro Asn Arg Pro Gly Gln Glu Lys Ser
        290                 295                 300
Val Pro Phe Ala Lys His Gln Ile Pro Leu Glu Ala Glu Ala Arg Ala
305                 310                 315                 320
Arg Asp Phe Leu His Asp Thr Met Pro His Leu Ala Asp Arg Pro Leu
                325                 330                 335
Ser Phe Ala Arg Ile Cys Trp Asp Asp Thr Pro Asp Arg Ala Phe
            340                 345                 350
Leu Ile Asp Arg His Pro Glu His Pro Ser Leu Leu Val Ala Val Gly
            355                 360                 365
Gly Ser Gly Asn Gly Ala Met Gln Met Pro Thr Ile Gly Gly Phe Ile
        370                 375                 380
Ala Asp Ala Leu Glu Ser Lys Leu Gln Lys Glu Val Lys Asp Ile Val
385                 390                 395                 400
Arg Trp Arg Pro Glu Thr Ala Val Asp Arg Asp Trp Arg Ala Thr Gln
                405                 410                 415
Asn Arg Phe Gly Gly Pro Asp Arg Ile Met Asp Phe Gln Gln Val Gly
            420                 425                 430
Glu Asp Gln Trp Thr Lys Ile Gly Glu Ser Arg Gly Pro
            435                 440                 445

<210> SEQ ID NO 2
<211> LENGTH: 1338
<212> TYPE: DNA
<213> ORGANISM: Artificial Sequence
<220> FEATURE:
<223> OTHER INFORMATION: cDNA Sequence Wild Type Amadoriase I

<400> SEQUENCE: 2
atggcgcctt caattttgag cactgaatct tccattatcg ttatcggagc aggcacatgg      60
ggctgctcaa ctgctctgca cctcgctcgt cgaggctaca agatgtcac tgttctcgac     120 cctcatccag ttccttcgcc cattgcagca ggcaatgaca tcaacaagat tatgagcac     180 agcgagctga agatggctc atccgaccct cgaagcgcag ccttctcgac atttacgcga     240
gctgctctta aggcgtggaa aactgacccg gttttccagc cttactttca cgaaactggc     300
tttatcatat cggggcacac acctgctctg attgaccaca tacgaaaaga cgaggtagaa     360
ccgtcagaaa caaacttcgt caagctggag acagccgagg acttccgccg gaccatgccg     420
ccaggtgtac tgacaggcga cttccctggc tggaaaggct ggttgcacaa gtctggtgct     480
gggtggattc atgccaaaaa ggctatgatc tctgctttca atgaagctaa gcgcttggga     540
gtcagatttg tcactggctc tccggaaggg aatgttgtat cgttggtata cgaggacgga     600
gacgtcgttg agccagaac tgccgatggt cgcgtgcaca agcccatcg cactattctt     660 tcggcaggtg ctggcagtga cagtctccta gacttcaaga agcagcttcg gcctaccgcg     720
tggactctct gtcatattca gatgggccct gaagaggtca gcaatatcg gaaccttcct     780 gtgttgttca acatcgccaa agggttcttc atggagcctg atgaggataa cacgagctc     840 aagatttgtg acgagcatcc agggtactgc aactttctcc ctgacccaaa cagaccgggc     900
caggagaaga gtgtccctt cgcaaagcat cagatcccgc tcgaggccga agcccgcgca     960
cgagactttc tccatgatac aatgccgcat ctggctgacc ggccactgtc tttcgcgcgt    1020
atttgctggg atgctgatac cccagaccgt gctttcttga tcgatagaca tcctgaacac    1080
```

| | |
|---|---|
| ccctcactgc tagtcgctgt tggaggttcc ggcaatggcg ccatgcaaat gcctacaatt | 1140 |
| ggcggtttta tcgcagatgc tctagagagt aaactacaga aggaggtgaa ggacatcgtt | 1200 |
| cgatggaggc cagagacggc tgtcgatcga gattggagag cgactcagaa tcgctttggc | 1260 |
| gggcctgaca ggatcatgga ttttcagcag gtcggagagg atcagtggac caagattgga | 1320 |
| gagagcagag gtccgtaa | 1338 |

<210> SEQ ID NO 3
<211> LENGTH: 1335
<212> TYPE: DNA
<213> ORGANISM: Artificial Sequence
<220> FEATURE:
<223> OTHER INFORMATION: cDNA Seq Wt Amad. I codon usage of E.coli

<400> SEQUENCE: 3

| | |
|---|---|
| atggctccga gcatcctgag caccgagagt tcgattattg tgatcggagc cggcacttgg | 60 |
| ggctgtagta cagcgcttca tttggctcgt cgtggctaca agatgtgac cgtgttagac | 120 |
| ccgcatccag ttccctcccc gattgcagcg ggcaatgata tcaacaaaat tatggaacac | 180 |
| agcgaactga agatggctc tagtgatcca cgctctgctg cattcagcac ctttacgcgc | 240 |
| gcggcgttga agcatggaa aaccgacccg gtatttcagc cgtatttca cgaaactggg | 300 |
| ttcatcatca gcggtcatac accggctctg attgatcata ttcgcaaaga tgaagttgaa | 360 |
| ccgtctgaaa ccaacttcgt gaaactcgag actgcggaag atttcgccg caccatgcct | 420 |
| cctggcgtcc tgacagggga cttccggggg tggaaaggct ggttgcacaa agtggtgcc | 480 |
| gggtggattc acgccaagaa agccatgatc tctgcgttta cgaagcaaa cgcctgggt | 540 |
| gttcgctttg tgaccggttc gccggaaggc aatgtagtgt ccctggtata cgaagatggc | 600 |
| gacgtcgttg gcgcccgtac cgctgatgga cgcgtgcata agcccaccg gaccattctg | 660 |
| tcagcaggcg cgggatcaga ttccctgtta gactttaaga agcagttacg tcccaccgct | 720 |
| tggacgttgt gccacatcca gatgggcccg gaagaagtta agcagtatcg caatctgccg | 780 |
| gtcctgttca acattgcgaa aggtttcttc atggaacctg atgaggacaa gcatgagctg | 840 |
| aaaatctgcg acgaacatcc agggtattgc aactttctcc cagacccgaa tcgtcccggt | 900 |
| caagagaaaa gcgtcccgtt cgcgaaacac cagatccctc ttgaggcgga agcacgtgcc | 960 |
| cgcgatttcc tccacgacac tatgccgcat ctggcagacc gcccttatc ctttgcgcgg | 1020 |
| atttgttggg atgccgatac gccggatcgg gcctttctga ttgaccgcca tcccgagcat | 1080 |
| ccgagcctgc tggtagccgt tggtggctca ggcaatggtg cgatgcaaat gccgacgatt | 1140 |
| ggtggattta tcgccgatgc gcttgaatcg aaactgcaga aggaagtgaa agacattgtc | 1200 |
| cgttggcgtc cagaaaccgc ggttgatcgc gattggcgtg caacgcagaa ccgttttggt | 1260 |
| ggtccggatc gcatcatgga tttccaacaa gtgggcgaag atcagtggac gaaaattggg | 1320 |
| gagtcgcgtg gtcca | 1335 |

<210> SEQ ID NO 4
<211> LENGTH: 445
<212> TYPE: PRT
<213> ORGANISM: Artificial Sequence
<220> FEATURE:
<223> OTHER INFORMATION: Amino acid sequence Amadoriase SS03 Ser67Cys + Pro121Cys

<400> SEQUENCE: 4

Met Ala Pro Ser Ile Leu Ser Thr Glu Ser Ser Ile Ile Val Ile Gly
1               5                   10                  15

```
Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
50                  55                  60

Asp Gly Cys Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Cys Ser Glu Thr Asn Phe Val Lys
            115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
            275                 280                 285

Tyr Cys Asn Phe Leu Pro Asp Pro Asn Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Ser Arg Ala Phe
            340                 345                 350

Leu Ile Asp Arg His Pro Glu His Pro Ser Leu Leu Val Ala Val Gly
            355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430
```

Glu Asp Gln Trp Thr Lys Ile Gly Glu Ser Arg Gly Pro
            435                 440                 445

<210> SEQ ID NO 5
<211> LENGTH: 1335
<212> TYPE: DNA
<213> ORGANISM: Artificial Sequence
<220> FEATURE:
<223> OTHER INFORMATION: DNA sequence Amadoriase SS03

<400> SEQUENCE: 5

```
atggctccga gcatcctgag caccgagagt tcgattattg tgatcggagc cggcacttgg      60
ggctgtagta cagcgcttca tttggctcgt cgtggctaca agatgtgac cgtgttagac     120
ccgcatccag ttccctcccc gattgcagcg ggcaatgata tcaacaaaat tatggaacac    180
agcgaactga agatggctg tagtgatcca cgctctgctg cattcagcac ctttacgcgc    240
gcggcgttga agcatggaa aaccgacccg gtatttcagc cgtattttca cgaaactggg    300
ttcatcatca gcggtcatac accggctctg attgatcata ttcgcaaaga tgaagttgaa    360
tgttctgaaa ccaacttcgt gaaactcgag actgcggaag attttcgccg caccatgcct    420
cctggcgtcc tgacagggga cttttccggg tggaaaggct ggttgcacaa agtggtgcc     480
gggtggattc acgccaagaa agccatgatc tctgcgttta cgaagcaaa cgcctgggt     540
gttcgctttg tgaccggttc gccggaaggc aatgtagtgt ccctggtata cgaagatggc    600
gacgtcgttg gcgcccgtac cgctgatgga cgcgtgcata agcccaccg gaccattctg    660
tcagcaggcg cgggatcaga ttccctgtta gactttaaga agcagttacg tcccaccgct    720
tggacgttgt gccacatcca gatgggcccg gaagaagtta gcagtatcg caatctgccg    780
gtcctgttca acattgcgaa aggtttcttc atggaacctg atgaggacaa gcatgagctg    840
aaaatctgcg acgaacatcc agggtattgc aactttctcc cagacccgaa tcgtcccggt    900
caagagaaaa cgtcccgtt cgcgaaacac cagatccctc ttgaggcgga agcacgtgcc    960
cgcgatttcc tccacgacac tatgccgcat ctggcagacc gcccttatc ctttgcgcgg   1020
atttgttggg atgccgatac gccggatcgg gcctttctga ttgaccgcca tcccgagcat   1080
ccgagcctgc tggtagccgt tggtggctca ggcaatggtg cgatgcaaat gccgacgatt   1140
ggtggattta cgccgatgc gcttgaatcg aaactgcaga aggaagtgaa agacattgtc   1200
cgttggcgtc cagaaaccgc ggttgatcgc gattggcgtg caacgcagaa ccgttttggt   1260
ggtccggatc gcatcatgga tttccaacaa gtgggcgaag atcagtggac gaaaattggg   1320
gagtcgcgtg gtcca                                                    1335
```

<210> SEQ ID NO 6
<211> LENGTH: 445
<212> TYPE: PRT
<213> ORGANISM: Artificial Sequence
<220> FEATURE:
<223> OTHER INFORMATION: Amino acid Sequence Amadoriase SS17 Asp295Cys +
      Lys303Cys

<400> SEQUENCE: 6

Met Ala Pro Ser Ile Leu Ser Thr Glu Ser Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

```
Ala Ala Gly Asn Asp Ile Asn Lys Ile Met Glu His Ser Glu Leu Lys
 50                  55                  60

Asp Gly Ser Ser Asp Pro Arg Ser Ala Ala Phe Ser Thr Phe Thr Arg
 65                  70                  75                  80

Ala Ala Leu Lys Ala Trp Lys Thr Asp Pro Val Phe Gln Pro Tyr Phe
                 85                  90                  95

His Glu Thr Gly Phe Ile Ile Ser Gly His Thr Pro Ala Leu Ile Asp
                100                 105                 110

His Ile Arg Lys Asp Glu Val Glu Pro Ser Thr Asn Phe Val Lys
            115                 120                 125

Leu Glu Thr Ala Glu Asp Phe Arg Arg Thr Met Pro Pro Gly Val Leu
130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
    195                 200                 205

Asp Gly Arg Val His Lys Ala His Arg Thr Ile Leu Ser Ala Gly Ala
210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Leu Pro Cys Pro Asn Arg Pro Gly Gln Glu Cys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
        435                 440                 445

<210> SEQ ID NO 7
<211> LENGTH: 1335
<212> TYPE: DNA
```

<213> ORGANISM: Artificial Sequence
<220> FEATURE:
<223> OTHER INFORMATION: DNA Sequence Amadoriase SS17

<400> SEQUENCE: 7

```
atggctccga gcatcctgag caccgagagt tcgattattg tgatcggagc cggcacttgg      60
ggctgtagta cagcgcttca tttggctcgt cgtggctaca aagatgtgac cgtgttagac     120
ccgcatccag ttccctcccc gattgcagcg ggcaatgata tcaacaaaat tatggaacac     180
agcgaactga aagatggctc tagtgatcca cgctctgctg cattcagcac ctttacgcgc     240
gcggcgttga agcatggaa aaccgacccg gtatttcagc cgtattttca cgaaactggg      300
ttcatcatca gcggtcatac accggctctg attgatcata ttcgcaaaga tgaagttgaa     360
ccgtctgaaa ccaacttcgt gaaactcgag actgcggaag attttcgccg caccatgcct     420
cctggcgtcc tgacagggga ctttccgggg tggaaaggct ggttgcacaa aagtggtgcc     480
gggtggattc acgccaagaa agccatgatc tctgcgttta cgaagcaaa acgcctgggt      540
gttcgctttg tgaccggttc gccggaaggc aatgtagtgt ccctggtata cgaagatggc     600
gacgtcgttg gcgcccgtac cgctgatgga cgcgtgcata agcccaccg gaccattctg      660
tcagcaggcg cgggatcaga ttccctgtta gactttaaga agcagttacg tcccaccgct     720
tggacgttgt gccacatcca gatgggcccg gaagaagtta agcagtatcg caatctgccg     780
gtcctgttca acattgcgaa aggtttcttc atggaacctg atgaggacaa gcatgagctg     840
aaaatctgcg acgaacatcc agggtattgc aactttctcc catgtccgaa tcgtcccggt     900
caagagtgta gcgtcccgtt cgcgaaacac cagatccctc ttgaggcgga agcacgtgcc     960
cgcgatttcc tccacgacac tatgccgcat ctggcagacc gcccttatc ctttgcgcgg     1020
atttgttggg atgccgatac gccggatcgg gcctttctga ttgaccgcca tcccgagcat    1080
ccgagcctgc tggtagccgt tggtggctca ggcaatggtg cgatgcaaat gccgacgatt    1140
ggtggattta tcgccgatgc gcttgaatcg aaactgcaga aggaagtgaa agacattgtc    1200
cgttggcgtc cagaaaccgc ggttgatcgc gattggcgtg caacgcagaa ccgttttggt    1260
ggtccggatc gcatcatgga tttccaacaa gtgggcgaag atcagtggac gaaaattggg    1320
gagtcgcgtg gtcca                                                    1335
```

US 11,649,440 B2

THERMOSTABILIZED AMADORIASES AND USES THEREOF

This application is a U.S. national stage of PCT/IB2018/054582 filed on 21 Jun. 2018 which claims priority to and the benefit of Italian patent application No. 102017000070452 filed on 23 Jun. 2017, the content of which are incorporated herein by reference in their entireties.

Sequence listing ASCII file sequence.txt, created on Feb. 26, 2021 and of size of 19.2 KB is incorporated herein by reference.

DESCRIPTION

The present invention refers to an Amadoriase enzyme having improved thermostability compared to the wild-type Amadoriase.

The present invention refers also to the use of the thermostabilized Amadoriase as deglycating agent, preferably in the food industry, such as milk pasteurization.

Moreover, the present invention refers to the use of the thermostabilized Amadoriase for determining the level of glycated haemoglobin in a biological sample and therefore for monitoring diabetes.

STATE OF THE ART

Glycation is the spontaneous, non-enzymatic and irreversible reaction that covalently adds a sugar moiety onto a protein.

The glycation of haemoglobin protein (HbA1c) is of particular interest for diabetes diagnosis and monitoring. The hyperglycemia associated with diabetes results in the non-enzymatic glycation of blood proteins, including haemoglobin (which has a half-life of 120 days) and albumin (half-life of 20 days). For this reason, the measurement of glycated haemoglobin in the blood is a very powerful method for monitoring the insurgence and development of diabetes. Indeed, while the direct blood sugar level measurement is affected by daily fluctuations, the long lifetime of haemoglobin combined with the slow, yet irreversible, glycation process makes the detection of HbA1c a good indicator of the average blood glucose concentration over a period of 2-3 months. For this reason, in 2010 the American Diabetes Association designated the level of HbA1c as a powerful indicator for the diagnosis of diabetes.

Since the assessment of glycated haemoglobin is becoming an indispensable part of diabetes diagnosis and control, the HbA1c test demands robustness, high-throughput, and cost effectiveness. As a result, several systems have been developed that are used in the clinics to measure HbA1c. Most methods rely on the separation of HbA1c from non-glycated haemoglobin based on their different chemical properties. These methods include ion exchange chromatography (based on the different isoelectric point), affinity chromatography (based on the different affinity for boronic acid) and capillary electrophoresis (based on the different charge). These current methods, while meeting the requirement for quality and robustness, are based on specialized and expensive techniques that require trained staff and thus fall short for cost-effectiveness and delivery at a point-of-care.

An Alternative Method for HbA1c Detection Exploits the Deglycating Properties of Amadoriases Amadoriase is a flavoenzyme that catalyzes the oxidative deglycation of Amadori products (fructosyl amino acids or aliphatic amines) to yield free amine, glucosone, and hydrogen peroxide.

Based on their activities, Amadoriases have been used to develop and commercialize a fast, easy and cost-effective HbA1c monitoring enzyme-based system (Direct Enzymatic HbA1c Assay, Diazyme Laboratories). Compared to chromatography- and electrophoresis-based sensing methods, the enzymatic assays have the advantage of being simple and inexpensive, hence good candidates for a point-of-care device. However, one of the issues of these enzyme sensors is their unsatisfactory absolute activity and stability. This issue affects storage stability against temperature changes, which in turn limits the applicability of enzymatic HbA1c monitoring systems based on enzymes.

In addition to the application of Amadoriase enzyme for HbA1c sensing, these enzymes have been proposed as a therapeutic tool for protein deglycation in the human body. However, since the wild type enzymes are able to act only on small substrates or digested proteins, extensive engineering will be necessary before their likely use as therapeutic tool.

Finally, glycation of food proteins is a drawback effect of several thermal treatment (e.g., milk UHT treatment), which results in alteration of the sensory and nutritional profile of the products. Amadoriase enzymes have a potential use in food industry in controlling and preventing protein glycation in food products, but the enzymes should be able to sustain the thermal treatments without losing activity.

There are many possible industrial applications where an increased stability of specific enzymes, such as Amadoriases, may be considered beneficial. Indeed, increasing the thermal and pH resistance of these enzymes can often greatly expand their natural operational range, thus allowing the use of engineered enzymes in environments that are unfavorable to their wildtype counterparts.

The present invention solves the needs of the prior art by identifying heat resistant variants of Amadoriase enzyme characterized by an improved thermal stability compared to the wild type enzyme. In particular, the heat resistant Amadoriase variants of the invention are characterized by specific amino acid changes/mutations that improve the foldability and the thermal stability of the wild type protein. Indeed, the identified heat resistant Amadoriase variants keep the 3D stability and are active up to 95° C., while the wild type protein is active only at less than 50° C.

SUMMARY OF THE INVENTION

A first aspect of the present invention refers to an isolated thermostable Amadoriase protein characterized by the replacement of amino acid serine in position 67 (S67) and/or proline in position 121 (P121) and/or aspartic acid in position 295 (D295) and/or lysine in position 303 (K303) with cysteine (C), wherein the amino acid position refers to the amino acid sequence of the wild type Amadoriase, that preferably has amino acid sequence SEQ ID NO: 1. Preferably, the mRNA/cDNA corresponding to SEQ ID NO: 1 is SEQ ID NO: 2 and/or SEQ ID NO: 3.

According to a preferred embodiment, the thermostable Amadoriase protein is characterized by an amino acid sequence comprising SEQ ID NO: 4 and/or 6. The isolated thermostable Amadoriase protein can be chemically modified in any way, preferably conjugated and/or flagged and/or marked, at the C-End and/or at the N-End, with metals, fluorophores, dyes, tags, reporters, wherein the tag is preferably selected from: a histidine-tag, a GST tag, and a MBP tag.

According to a preferred embodiment, the polynucleotide sequence codifying the isolated thermostable Amadoriase protein of the invention is preferably SEQ ID NO: 5 and/or 7.

A further aspect of the invention refers to a derivative from isolated thermostable Amadoriase protein of the invention or from polynucleotide sequence thereof, preferably said derivative being selected from: an oligopeptide, a peptide/oligopeptide, and any engineered Amadoriase mutant/variant carrying at least one of the replacement disclosed above, preferably the replacement of amino acid serine in position 67 (S67) and/or proline in position 121 (P121) and/or aspartic acid in position 295 (D295) and/or lysine in position 303 (K303) with cysteine (C).

A further aspect of the invention refers to a crystal or isomorph of the isolated thermostable Amadoriase protein of the invention.

A further aspect of the invention refers recombinant vector or a host cell comprising and/or transformed/transfected with the recombinant vector comprising the polynucleotide sequence of the invention.

A further aspect of the invention refers to the use of the isolated thermostable Amadoriase protein of the invention to de-glycate molecules and/or proteins, wherein said molecules/proteins are preferably from animal and/or human body or from foods.

A further aspect of the invention refers to the use of the isolated thermostable Amadoriase protein of the invention in food industry, preferably for thermal treatments, preferably selected from: milk UHT treatment, any treatment causing the glycation of food proteins and/or the loss of organoleptic and/or quality profile of food.

A further aspect of the invention refers to the use of the isolated thermostable Amadoriase protein, or the polynucleotide sequence, or the derivative, or the crystal or isomorph of the invention as therapeutic tool, preferably to reduce the in vivo glycation of molecules and/or proteins.

Moreover, the invention refers to the use of the isolated thermostable Amadoriase protein, or the polynucleotide sequence, or the derivative, or the crystal or isomorph of the invention as diagnostic tool and/or biosensor, preferably to detect glycated hemoglobin and/or to monitor the insurgence and/or the development diabetes, preferably diabetes mellitus.

A further aspect of the invention refers to a kit for detecting glycated hemoglobin and/or for evaluating/measuring diabetes, preferably diabetes mellitus comprising the isolated thermostable Amadoriase protein, or the polynucleotide sequence, or the derivative, or the crystal or isomorph of the invention.

Finally, the invention refers also to a method for measuring glycated haemoglobin in a biologic sample, preferably in blood, and/or for determining the insurgence and/or the development of diabetes, preferably diabetes mellitus said method comprising the following steps:

(i) Digesting a sample comprising heamoglobin to proteases in order to release amino acids, preferably the glycated valine from the N-terminus of haemoglobin;

(ii) Deglycating the valine released according to step (i) by adding the thermostable Amadoriase protein variants disclosed above; and (iii) Measuring/determining the amount of hydrogen peroxide produced after step (ii).

SHORT DESCRIPTION OF DRAWINGS

FIG. 1 shows Amadoriase I enzyme and the selected mutations. The wild type Amadoriase I is shown in cartoon representation, while the residues mutated to cysteine in the SS-variants are represented in sticks (for SS03 residues S67 and P121, for SS17 residues D295 and K303).

Figure 2:
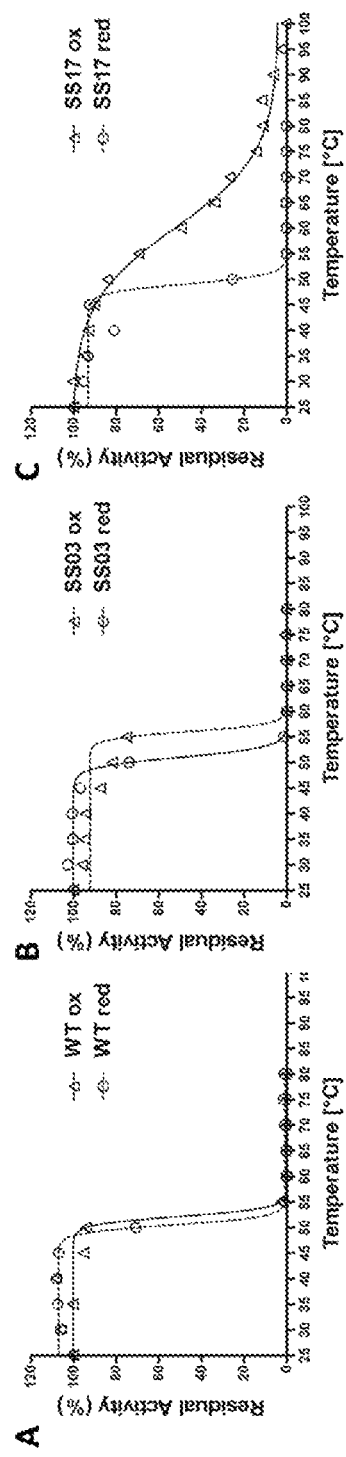

FIG. 2 shows the thermostabilization of Amadoriase variants. The residual activity of the oxidized form of the enzymes is shown with triangles (Bolzmann fitting with continuous line). The residual activity of the reduced form is shown for each enzyme with empty circles (Bolzmann fitting curves with dashed lines).

DETAILED DESCRIPTION OF THE INVENTION

A first aspect of the present invention refers to an isolated thermostable Amadoriase protein characterized by the substitution (mutation/alteration/replacement) of amino acid serine in position 67 (S67) and/or proline in position 121 (P121) and/or aspartic acid in position 295 (D295) and/or lysine in position 303 (K303) with cysteine (C), wherein the amino acid position refers to the amino acid sequence of the wild type Amadoriase, that preferably has amino acid sequence SEQ ID NO: 1. Preferably the mRNA/cDNA corresponding to SEQ ID NO: 1 is SEQ ID NO: 2.

Amadoriases, also known as fructosyl amine oxidases (abbreviated as FAOX or FAOD), are a family of enzymes derived from fungi and bacteria that are able to cleave low molecular weight Amadori product (i.e, glycated amino acids) to yield a free amine, glucosone, and hydrogen peroxide. At present, this enzyme family is composed of around 15 different forms as summarized in Table 1, which share common structural features, such as FAD-binding motifs. The physiological role of eukaryotic FAODs remains unknown, while extensive studies showed that prokaryotic FAOD as the key enzyme in the catabolic pathway of naturally occurring fructosyl amino acids. In this context, Amadoriase is preferably Amadoriase I. Moreover, as already mentioned, in the context of the present invention, the amino acid sequence of the wild type Amadoriase is preferably SEQ ID NO: 1 and the corresponding mRNA/cDNA is SEQ ID NO: 2. The position of the amino acid residues modified according to the present invention is calculated considering SEQ ID NO: 1 as reference sequence. However, the variants derived from the modification(s)/mutation(s) of the corresponding amino acid residues on the sequence of the different (known) forms of the Amadoriase enzyme family are part of this disclosure.

Preferably, the Amadoriases of the present invention are from any source, preferably from eukaryotes, more preferably from fungi, still more preferably of genera *Aspergillus*, still more preferably the *Asperigillus* species *fumigatus*.

TABLE 1

Properties of fructosyl amine oxidases

| Organism type | Source | Enzyme Abbreviation | Molecular mass (kDa) | Monomer/Dimer | Substrate specificity group |
|---|---|---|---|---|---|
| Prokaryotic | *Corynebacterium* sp. 2-4-1 | FAOX-C | 44 | dimer | Group 1 Prefer α-fructosyl amino acids (e.g., f-$^{\alpha}$Val) |
| | *Agrobacterium tumefaciens* | AgaE-like protein | 42 | dimer | |
| | *Arthrobacter* sp. FV1-1 | FAOD-Ar | 39 | dimer | |
| | *Aspergillus* sp. 1005 | FAOX | 43 | dimer | |
| | *Penicillium janthinellum* AKU3413 | FAOD-P | 39-49 | monomer | |
| | *Eupenicillium terrenum* ATCC 18547 | FPOX-E | 50 | monomer | |
| | *Coniochaeta* sp. NISL 9330 | FPOX-C | 52-60 | monomer | |
| | *Fusarium oxysporum* S-1F4 | FLOD | 45-50 | monomer | Group II Prefer ε-fructosyl amino acids (e.g., f-$^{\epsilon}$Lys) |
| Eukaryotic | *Fusarium oxysporum* IFO-9972 | FOD-F | 47-48 | monomer | |
| | *Aspergillus fumigatus* | Amadoriase I | 40-51 | monomer | |
| | *Aspergillus oryzae* | FAOD-A01 | 39-49 | monomer | |
| | *Pichia* sp. N1-1 | FAOD-Pi | 54 | monomer | Group III React with both α- and ε-fructosyl amino acids |
| | *Aspergillus fumigatus* | Amadoriase II | 49-55 | monomer | |
| | *Aspergillus oryzae* | FAOD-A02 | 48 | dimer | |
| | *Aspergillus terreus* GP1 | FAOD-A | 51 | dimer | |

Amadoriases are currently used as biosensors meaning that they are used to detect glycated proteins, such as hemoglobin to monitor diabetes. These enzymes have also been proposed to be used as a therapeutic tool to reduce in vivo glycation.

Finally, Amadoriase enzymes have a potential use also in the food industry, preferably to control and/or to prevent protein glycation in food products, preferably during and after heat treatment of food products, for example milk pasteurization.

The new protein variants of Amadoriase enzyme having the mutation(s) reported above are characterized by an improved heat resistance. In other words, they show a better thermostability compared to the wild type Amadoriase enzyme. In this regard, indeed, as well demonstrated and explained in the examples below, while the wild type protein is stable, and consequently functional and/or biologically active, at temperature values less than 50° C., the Amadoriase variants of the present invention keep their stability and functionality at a temperature up to 95, preferably up to 90° C., more preferably up to 80° C. In particular, the Amadoriase variants of the present invention show an improved $T_{50}$, that is the temperature at which the enzyme loses 50% of the activity compared to the activity at 25° C. The thermostable Amadoriase variants of the invention show preferably a $T_{50}$ ranging from 50° C. to 70° C., more preferably from 55° C. to 60° C., still more preferably from 55.3° C. and 60.6° C. Preferably, SS03 shows the minimum value of $T_{50}$ while SS17 the maximum. Preferably, the wild-type enzyme presents a $T_{50}$ of around 50° C., more preferably 52, still more preferably 52.4° C. Preferably, the disclosed values of $T_{50}$ are referred to the experimental conditions of the invention.

Moreover, advantageously the Amadoriase variants of the present invention are characterized by an improved shelf life and/or longer expiry date/time storage.

In view of these features, the Amadoriase variants of the present invention are ideal to be used as molecular components of processes involving heat treatments and/or to preserve the integrity and/or provides long-term stability to samples by preventing amino acid glycation.

Moreover, the Amadoriase variants of the present invention are ideal to be used in food industry. Examples of specific applications in this field are: milk pasteurization, production of bakery products or treatment of food additives, preferably artificial sweeteners or flavor enhancers.

Moreover, the Amadoriase variants of the present invention can be used in the pharmaceutical or cosmetic industry, preferably for drug formulation or thermal treatment of pharmaceutical excipients.

As mentioned before, the Amadoriase protein variants of the present invention are characterized by a protein sequence having the substitution (mutation/alteration/replacement) of amino acid serine in position 67 (S67) and/or proline in position 121 (P121) and/or aspartic acid in position 295 (D295) and/or lysine in position 303 (K303) with cysteine (C), wherein the amino acid position refers to the amino acid sequence of the wild type Amadoriase, preferably SEQ ID NO: 1.

These Amadoriase variants show de-glycating activity and an improved thermostability compared to the wild type enzyme (the Amadoriase variants of the invention are stable at a temperature up to 95° C., preferably up to 90° C., more preferably up to 80° C., while the wild type is stable at a temperature less than 55° C.).

In the context of the present invention, "substitution of amino acid" means to modify or to mutate in the context of a protein/peptide sequence an amino acid into another. In this case, the amino acid(s) of interest is(are) mutated, singularly or in any combinations, into cysteine. In particular, the codons on the cDNA/mRNA sequence of the protein corresponding to the amino acid residues have been modified through genetic engineering techniques so that the translated proteins contain the mutation.

SEQ ID NO: 1 is preferably the sequence of the wild type amodoriase enzyme. SEQ ID NO: 2 is preferably the corresponding mRNA/cDNA sequence. The specific amino acid residues of SEQ ID NO: 1 (serine 67 and/or proline 121 and/or aspartic acid 295 and/or lysine 303) eventually modified in cysteine individually or in any combinations according to the invention are bold-underlined in Table I wherein all the all the sequences disclosed in the present application are listed.

The present invention refers also to SEQ ID NO: 3 that is the cDNA sequence optimized for the *E. coli* expression (Codon Optimized—CO); in other words SEQ ID NO: 3 is SEQ ID NO: 2 modified according to the codon usage of *E. coli* in order to boost the expression of the protein in this bacterium.

According to a preferred embodiment of the invention, the isolated thermostable Amadoriase protein variant is characterized by the substitution (mutation) of the amino acid serine in position 67 and the proline in position 121 with a cysteine wherein the amino acid position refers to the amino acid sequence of the wild type Amadoriase, preferably SEQ ID NO: 1. This variant is named Amadoriase SS03 from now on and it is characterized by the following mutation/substitution Ser67Cys and Pro121Cys. Amadoriase SS03 is characterized by a protein 3D structure (the folded protein) having an additional disulfide bond between the mutated residues mentioned above (FIG. 1), that are the cysteine (instead of the wild type serine) in position 67 and the cysteine in position 121 (instead of the wild type proline).

According to a further preferred embodiment of the invention, the isolated thermostable Amadoriase protein variant is characterized by the substitution (mutation) of the amino acid aspartic acid in position 295 and the lysine in position 303 with a cysteine wherein the amino acid position refers to the amino acid sequence of the wild type Amadoriase, preferably SEQ ID NO: 1. This variant is named Amadoriase SS17 from now on and it is characterized by the following mutation/substitution Asp295Cys and Lys303Cys. Amadoriase SS17 is characterized by a protein 3D structure (the folded protein) having an additional disulfide bond between the mutated residues mentioned above (FIG. 1), that are the cysteine (instead of the wild type aspartic acid) in position 295 and the cysteine in position 303 (instead of the wild type lysine).

According to a preferred embodiment of the invention, the isolated thermostable Amadoriase protein variant is characterized by the substitution (mutation) of amino acid serine in position 67, proline in position 121, aspartic acid in position 295 and lysine in position 303 (each one) with a cysteine wherein the amino acid position refers to the amino acid sequence of the wild type Amadoriase, preferably SEQ ID NO: 1. This Amadoriase variant is characterized by a protein 3D structure (the folded protein) having two additional disulfide bonds between the mutated residues mentioned above (one between cysteine in position 67 and cysteine in position 121 and another between cysteine in position 295 and cysteine in position 303).

According to a further preferred embodiment of the invention, the isolated thermostable Amadoriase protein variant is characterized by an amino acid sequence comprising SEQ ID NO: 4 and/or 6. As already mentioned for SEQ ID NO: 1-3, SEQ ID NO: 4 and 6 are listed in Table I and the mutated/modified amino acid residues are marked as bold-underlined.

SEQ ID NO: 4 corresponds to the amino acid (protein) sequence of the Amadoriase comprising a mutation/substitution from serine in position 67 and proline 121 to cysteine (Ser67Cys and Pro121Cys) wherein the amino acid position refers to the amino acid sequence of the wild type Amadoriase, preferably SEQ ID NO: 1. This Amadoriase variant is named SS03.

SEQ ID NO: 6 corresponds to the amino acid (protein) sequence of the Amadoriase variant comprising a mutation/substitution from aspartic acid in position 295 and lysine in position 303 to cysteine (Asp295Cys and Lys303Cys) wherein the amino acid position refers to the amino acid sequence of the wild type Amadoriase, preferably SEQ ID NO: 1. This Amadoriase variant is named SS17.

A further aspect of the present invention, refers to a polynucleotide sequence codifying the isolated thermostable Amadoriase protein variants as disclosed above, preferably said polynucleotide sequence being SEQ ID NO: 5 and/or 7, wherein SEQ ID NO: 5 corresponds to the polynucleotide sequence codifying the Amadoriase SS03 variant, while SEQ ID NO: 7 corresponds to the polynucleotide sequence codifying the Amadoriase SS17 variant.

SEQ ID NO: 5 and 7 are listed in Table I and the codons (the trinucleotides codifying for the amino acid residues) corresponding to the amino acid residues mutated/modified according to the invention are marked bold-underlined.

The present invention refers also to any derivative from the thermostable Amadoriase variants disclosed above, preferably oligopeptides, peptides, or further engineered Amadoriase mutants carrying one and/or both the disulfide bonds described herein.

A further aspect of the present invention refers to the protein crystal of the isolated thermostable Amadoriase protein variants disclosed above, preferably of SS03 and/or SS17 Amadoriase variant(s).

Alternatively, the thermostable Amadoriase proteins of the invention can be chemically modified in any way, preferably they can be conjugated and/or flagged and/or marked with metals, fluorophores, dyes, tags, reporters. Only as an example, the thermostable Amadoriase proteins can be tagged by introducing, at the C-terminus and/or at the N-terminus, a histidine-tag, a GST tag, a MBP tag, one or more N-terminal or C-terminal cysteines or any further tag, in order to facilitate the purification step of the proteins from the host cells and/or to conjugate the protein onto a natural and/or chemically modified surface.

A further aspect of the present invention refers to a recombinant vector comprising the polynucleotide sequence codifying the isolated thermostable Amadoriase protein variants, said polynucleotide sequence being preferably SEQ ID NO: 5 and/or 7. Preferably, the recombinant vector is any vector useful for the posed scope and known to the skilled in the art, more preferably the vector is from pET generation, more preferably pET3a.

A further aspect of the present invention refers to a host cell comprising and/or transformed/transfected with the recombinant vector disclosed above and/or permanently expressing the thermostable Amadoriase protein variants of the invention. The host cell is preferably selected from: bacteria, preferably *E. coli*, more preferably the strain BL21 (DE3) and/or BL21(DE3)pLysS, yeasts, eukaryotic cells and insect cells.

A further aspect of the invention refers to a method for producing the thermostable Amadoriase protein variants of the invention comprising at least one of the following steps:

(i) culturing host cells comprising and/or transformed/transfected by using the recombinant vector disclosed above and/or permanently expressing the thermostable Amadoriase protein variants of the invention, and (ii) collecting the thermostable Amadoriase protein variants said thermostable Amadoriase protein variants having preferably de-glycating activity and/or a thermostability up to 95° C., preferably up to 90° C., more preferably up to 80° C.

The thermostable Amadoriase protein variants collected according to step (ii) can be purified (purifying step) by using the canonical processes used to this end.

Table I lists the sequences herein disclosed. In particular, it shows the specific sequence, the name of the sequence and the corresponding SEQ ID NO. The sequences are also provided with a Sequence Listing generated by using PatentIn software. Any sequence having 80-99% identity with the sequences hereby disclosed should be considered part of the invention.

TABLE I

| SEQUENCE | NAME | SEQ ID NO |
|---|---|---|
| MAPSILSTESSIIVIGAGTVVGCSTALHLARRGYKDVTVLDPHPV PSPIAAGNDINKIMEHSELKDGSSDPRSAAFSTFTRAALKAWK TDPVFQPYFHETGFIISGHTPALIDHIRKDEVEPSETNFVKLETA EDFRRTMPPGVLTGDFPGWKGWLHKSGAGWIHAKKAMISAF NEAKRLGVRFVTGSPEGNVVSLVYEDGDVVGARTADGRVHK AHRTILSAGAGSDSLLDFKKQLRPTAWTLCHIQMGPEEVKQY RNLPVLFNIAKGFFMEPDEDKHELKICDEHPGYCNFLPDPNRP GQEKSVPFAKHQIPLEAEARARDFLHDTMPHLADRPLSFARIC WDADTPDRAFLIDRHPEHPSLLVAVGGSGNGAMQMPTIGGFI ADALESKLQKEVKDIVRWRPETAVDRDWRATQNRFGGPDRI MDFQQVGEDQWTKIGESRGP | Amino acid Sequence Wild Type Amadoriase I | SEQ ID NO: 1 |
| ATG GCG CCT TCA ATT TTG AGC ACT GAA TCT TCC ATT ATC GTT ATC GGA GCA GGC ACA TGG GGC TGC TCA ACT GCT CTG CAC CTC GCT CGT CGA GGC TAC AAA G AT GTC ACT GTT CTC GAC CCT CAT CCA GTT CCT TCG CCC ATT GCA GCA GGC AAT GAC ATC AAC AAG ATT ATG GAG CAC AGC GAG CTG AAA GAT GGC TCA TCC GAC CCT CGA AGC GCA GCC TTC TCG ACA TTT ACG CGA GCT GCT CTT AAG GCG TGG AAA ACT GAC CCG GTT TTC CAG CCT TAC TTT CAC GAA ACT GGC TTT ATC ATA TCG GGG CAC ACA CCT GCT CTG ATT GAC CAC ATA CGA AAA GAC GAG GTA GAA CCG TCA GAA ACA AAC TTC GTC AAG CTG GAG ACA GCC GAG GAC TTC CGC CGG ACC ATG CCG CCA GGT GTA CTG ACA GGC GAC TTC CCT GGC TGG AAA GGC TGG TTG CAC AAG TCT GGT GCT GGG TGG ATT CAT GCC AAA AAG GCT ATG ATC TCT GCT TTC AAT GAA GCT AAG CGC TTG GGA GTC AGA TTT GTC ACT GGC TCT CCG GAA GGG AAT GTT GTA TCG TTG GTA TAC GAG GAC GGA GAC GTC GTT GGA GCC AGA ACT GCC GAT GGT CGC GTG CAC AAA GCC CAT CGC ACT ATT CTT TCG GCA GGT GCT GGC AGT GAC AGT CTC CTA GAC TTC AAG AAG CAG CTT CGG CCT ACC GCG TGG ACT CTC TGT CAT ATT CAG ATG GGC CCT GAA GAG GTC AAG CAA TAT CGG AAC CTT CCT GTG TTG TTC AAC ATC GCC AAA GGG TTC TTC ATG GAG CCT GAT GAG GAT AAA CAC GAG CTC AAG ATT TGT GAC GAG CAT CCA GGG TAC TGC AAC TTT CTC CCT GAC CCA AAC AGA CCG GGC CAG GAG AAG AGT GTC CCC TTC GCA AAG CAT CAG ATC CCG CTC GAG GCC GAA GCC CGC GCA CGA GAC TTT CTC CAT GAT ACA ATG CCG CAT CTG GCT GAC CGG CCA CTG TCT TTC GCG CGT ATT TGC TGG GAT GCT GAT ACC CCA GAC CGT GCT TTC TTG ATC GAT AGA CAT CCT GAA CAC CCC TCA CTG CTA GTC GCT GTT GGA GGT TCC GGC AAT GGC GCC ATG CAA ATG CCT ACA ATT GGC GGT TTT ATC GCA GAT GCT CTA GAG AGT AAA CTA CAG AAG GAG GTG AAG GAC ATC GTT CGA TGG AGG CCA GAG ACG GCT GTC GAT CGA GAT TGG AGA GCG ACT CAG AAT CGC TTT GGC GGG CCT GAC AGG ATC ATG GAT TTT CAG CAG GTC GGA GAG GAT CAG TGG ACC AAG ATT GGA GAG AGC AGA GGT CCG TAA | cDNA Sequence Wild Type Amadoriase I | SEQ ID NO: 2 |
| ATG GCT CCG AGC ATC CTG AGC ACC GAG AGT TCG ATT ATT GTG ATC GGA GCC GGC ACT TGG GGC TGT AGT ACA GCG CTT CAT TTG GCT CGT CGT GGC TAC AAA GAT GTG ACC GTG TTA GAC CCG CAT CCA GTT CCC TCC CCG ATT GCA GCG GGC AAT GAT ATC AAC AAA ATT ATG GAA CAC AGC GAA CTG AAA GAT GGC TCT AGT GAT CCA CGC TCT GCT GCA TTC AGC ACC TTT ACG CGC GCG GCG TTG AAA GCA TGG AAA ACC GAC CCG GTA TTT CAG CCG TAT TTT CAC GAA ACT GGG TTC ATC ATC AGC GGT CAT ACA CCG GCT CTG ATT GAT CAT ATT CGC AAA GAT GAA GTT GAA CCG TCT GAA ACC AAC TTC GTG AAA CTC GAG ACT GCG GAA GAT TTT CGC CGC ACC ATG CCT CCT GGC GTC CTG ACA GGG GAC TTT CCG GGG TGG AAA GGC TGG TTG CAC AAA AGT GGT GCC GGG TGG ATT CAC GCC AAG AAA GCC ATG ATC TCT GCG TTT AAC GAA GCA AAA CGC CTG GGT GTT CGC TTT GTG ACC GGT TCG CCG GAA GGC AAT GTA GTG TCC CTG GTA TAC GAA GAT GGC GAC GTC GTT | cDNA Sequence Wild Type Amadoriase I codon usage of E. coli | SEQ ID NO: 3 |

TABLE I-continued

| SEQUENCE | NAME | SEQ ID NO |
|---|---|---|
| GGC GCC CGT ACC GCT GAT GGA CGC GTG CAT AAA<br>GCC CAC CGG ACC ATT CTG TCA GCA GGC GCG GGA<br>TCA GAT TCC CTG TTA GAC TTT AAG AAG CAG TTA CGT<br>CCC ACC GCT TGG ACG TTG TGC CAC ATC CAG ATG GGC<br>CCG GAA GAA GTT AAG CAG TAT CGC AAT CTG CCG GTC<br>CTG TTC AAC ATT GCG AAA GGT TTC TTC ATG GAA CCT<br>GAT GAG GAC AAG CAT GAG CTG AAA ATC TGC GAC GAA<br>CAT CCA GGG TAT TGC AAC TTT CTC CCA GAC CCG AAT<br>CGT CCC GGT CAA GAG AAA AGC GTC CCG TTC GCG AAA<br>CAC CAG ATC CCT CTT GAG GCG GAA GCA CGT GCC<br>CGC GAT TTC CTC CAC GAC ACT ATG CCG CAT CTG GCA<br>GAC CGC CCT TTA TCC TTT GCG CGG ATT TGT TGG GAT<br>GCC GAT ACG CCG GAT CGG GCC TTT CTG ATT GAC CGC<br>CAT CCC GAG CAT CCG AGC CTG CTG GTA GCC GTT GGT<br>GGC TCA GGC AAT GGT GCG ATG CAA ATG CCG ACG ATT<br>GGT GGA TTT ATC GCC GAT GCG CTT GAA TCG AAA CTG<br>CAG AAG GAA GTG AAA GAC ATT GTC CGT TGG CGT CCA<br>GAA ACC GCG GTT GAT CGC GAT TGG CGT GCA ACG<br>CAG AAC CGT TTT GGT GGT CCG GAT CGC ATC ATG GAT<br>TTC CAA CAA GTG GGC GAA GAT CAG TGG ACG AAA ATT<br>GGG GAG TCG CGT GGT CCA | | |
| MAPSILSTESSIIVIGAGTWGCSTALHLARRGYKDVTVLDPHPV<br>PSPIAAGNDINKIMEHSELKDGCSDPRSAAFSTFTRAALKAWK<br>TDPVFQPYFHETGFIISGHTPALIDHIRKDEVECSETNFVKLETA<br>EDFRRTMPPGVLTGDFPGWKGWLHKSGAGWIHAKKAMISAF<br>NEAKRLGVRFVTGSPEGNVVSLVYEDGDVVGARTADGRVHK<br>AHRTILSAGAGSDSLLDFKKQLRPTAWTLCHIQMGPEEVKQY<br>RNLPVLFNIAKGFFMEPDEDKHELKICDEHPGYCNFLPDPNRP<br>GQEKSVPFAKHQIPLEAEARARDFLHDTMPHLADRPLSFARIC<br>WDADTPDRAFLIDRHPEHPSLLVAVGGSGNGAMQMPTIGGFI<br>ADALESKLQKEVKDIVRWRPETAVDRDWRATQNRFGGPDRI<br>MDFQQVGEDQWTKIGESRGP | Amino acid<br>sequence<br>Amadoriase<br>SS03<br>Ser67Cys +<br>Pro121Cys | SEQ ID NO: 4 |
| ATGGCTCCGAGCATCCTGAGCACCGAGAGTTCGATTATTGT<br>GATCGGAGCCGGCACTTGGGGCTGTAGTACAGCGCTTCAT<br>TTGGCTCGTCGTGGCTACAAAGATGTGACCGTGTTAGACC<br>CGCATCCAGTTCCCTCCCCGATTGCAGCGGGCAATGATAT<br>CAACAAAATTATGGAACACAGCGAACTGAAAGATGGCTGTA<br>GTGATCCACGCTCTGCTGCATTCAGCACCTTTACGCGCGC<br>GGCGTTGAAAGCATGGAAAACCGACCCGGTATTTCAGCCG<br>TATTTTCACGAAACTGGGTTCATCATCAGCGGTCATACACC<br>GGCTCTGATTGATCATATTCGCAAAGATGAAGTTGAATGTT<br>CTGAAACCAACTTCGTGAAACTCGAGACTGCGGAAGATTTT<br>CGCCGCACCATGCCTCCTGGCGTCCTGACAGGGGACTTTC<br>CGGGGTGGAAAGGCTGGTTGCACAAAAGTGGTGCCGGGT<br>GGATTCACGCCAAGAAAGCCATGATCTCTGCGTTTAACGAA<br>GCAAAACGCTGGGTGTTCGCTTTGTGACCGGTTCGCCGG<br>AAGGCAATGTAGTGTCCCTGGTATACGAAGATGGCGACGT<br>CGTTGGCGCCCGTACCGCTGATGGACGCGTGCATAAAGCC<br>CACCGGACCATTCTGTCAGCAGGCGCGGGATCAGATTCCC<br>TGTTAGACTTTAAGAAGCAGTTACGTCCCACCGCTTGGACG<br>TTGTGCCACATCCAGATGGGCCCGGAAGAAGTTAAGCAGT<br>ATCGCAATCTGCCGGTCCTGTTCAACATTGCGAAAGGTTTC<br>TTCATGGAACCTGATGAGGACAAGCATGAGCTGAAAATCTG<br>CGACGAACATCCAGGGTATTGCAACTTTCTCCCAGACCCGA<br>ATCGTCCCGGTCAAGAGAAAAGCGTCCCGTTCGCGAAACA<br>CCAGATCCCTCTTGAGGCGGAAGCACGTGCCCGCGATTTC<br>CTCCACGACACTATGCCGCATCTGGCAGACCGCCCTTTATC<br>CTTTGCGCGGATTTGTTGGGATGCCGATACGCCGGATCGG<br>GCCTTTCTGATTGACCGCCATCCCGAGCATCCGAGCCTGC<br>TGGTAGCCGTTGGTGGCTCAGGCAATGGTGCGATGCAAAT<br>GCCGACGATTGGTGGATTTATCGCCGATGCGCTTGAATCG<br>AAACTGCAGAAGGAAGTGAAAGACATTGTCCGTTGGCGTC<br>CAGAAACCGCGGTTGATCGCGATTGGCGTGCAACGCAGAA<br>CCGTTTTGGTGGTCCGGATCGCATCATGGATTTCCAACAAG<br>TGGGCGAAGATCAGTGGACGAAAATTGGGGAGTCGCGTGG<br>TCCA | DNA<br>sequence<br>Amadoriase<br>SS03 | SEQ ID NO: 5 |
| MAPSILSTESSIIVIGAGTWGCSTALHLARRGYKDVTVLDPHPV<br>PSPIAAGNDINKIMEHSELKDGSSDPRSAAFSTFTRAALKAWK<br>TDPVFQPYFHETGFIISGHTPALIDHIRKDEVEPSETNFVKLETA<br>EDFRRTMPPGVLTGDFPGWKGWLHKSGAGWIHAKKAMISAF<br>NEAKRLGVRFVTGSPEGNVVSLVYEDGDVVGARTADGRVHK<br>AHRTILSAGAGSDSLLDFKKQLRPTAWTLCHIQMGPEEVKQY<br>RNLPVLFNIAKGFFMEPDEDKHELKICDEHPGYCNFLPCPNRP<br>GQECSVPFAKHQIPLEAEARARDFLHDTMPHLADRPLSFARIC<br>WDADTPDRAFLIDRHPEHPSLLVAVGGSGNGAMQMPTIGGFI | Amino acid<br>Sequence<br>Amadoriase<br>SS17<br>Asp295Cys +<br>Lys303Cys | SEQ ID NO: 6 |

TABLE I-continued

| SEQUENCE | NAME | SEQ ID NO |
|---|---|---|
| ADALESKLQKEVKDIVRWRPETAVDRDWRATQNRFGGPDRI MDFQQVGEDQWTKIGESRGP | | |
| ATGGCTCCGAGCATCCTGAGCACCGAGAGTTCGATTATTGT GATCGGAGCCGGCACTTGGGGCTGTAGTACAGCGCTTCAT TTGGCTCGTCGTGGCTACAAAGATGTGACCGTGTTAGACC CGCATCCAGTTCCCTCCCCGATTGCAGCGGGCAATGATAT CAACAAAATTATGGAACACAGCGAACTGAAAGATGGCTCTA GTGATCCACGCTCTGCTGCATTCAGCACCTTTACGCGCGC GGCGTTGAAAGCATGGAAAACCGACCCGGTATTTCAGCCG TATTTTCACGAAACTGGGTTCATCATCAGCGGTCATACACC GGCTCTGATTGATCATATTCGCAAAGATGAAGTTGAACCGT CTGAAACCAACTTCGTGAAACTCGAGACTGCGGAAGATTTT CGCCGCACCATGCCTCCTGGCGTCCTGACAGGGGACTTTC CGGGGTGGAAAGGCTGGTTGCACAAAAGTGGTGCCGGGT GGATTCACGCCAAGAAAGCCATGATCTCTGCGTTTAACGAA GCAAAACGCCTGGGTGTTCGCTTTGTGACCGGTTCGCCGG AAGGCAATGTAGTGTCCCTGGTATACGAAGATGGCGACGT CGTTGGCGCCCGTACCGCTGATGGACGCGTGCATAAAGCC CACCGGACCATTCTGTCAGCAGGCGCGGGATCAGATTCCC TGTTAGACTTTAAGAAGCAGTTACGTCCCACCGCTTGGACG TTGTGCCACATCCAGATGGGCCCGGAAGAAGTTAAGCAGT ATCGCAATCTGCCGGTCCTGTTCAACATTGCGAAAGGTTTC TTCATGGAACCTGATGAGGACAAGCATGAGCTGAAAATCTG CGACGAACATCCAGGGTATTGCAACTTTCTCCCATGTCCGA ATCGTCCCGGTCAAGAGTGTAGCGTCCCGTTCGCGAAACA CCAGATCCCTCTTGAGGCGGAAGCACGTGCCCGCGATTTC CTCCACGACACTATGCCGCATCTGGCAGACCGCCCTTTATC CTTTGCGCGGATTTGTTGGGATGCCGATACGCCGGATCGG GCCTTTCTGATTGACCGCCATCCCGAGCATCCGAGCCTGC TGGTAGCCGTTGGTGGCTCAGGCAATGGTGCGATGCAAAT GCCGACGATTGGTGGATTTATCGCCGATGCGCTTGAATCG AAACTGCAGAAGGAAGTGAAAGACATTGTCCGTTGGCGTC CAGAAACCGCGGTTGATCGCGATTGGCGTGCAACGCAGAA CCGTTTTGGTGGTCCGGATCGCATCATGGATTTCCAACAAG TGGGCGAAGATCAGTGGACGAAAATTGGGGAGTCGCGTGG TCCA | DNA Sequence Amadoriase SS17 | SEQ ID NO: 7 |

A further aspect of the present invention refers to the use of the thermostable Amadoriase protein variants disclosed above to de-glycate molecules, preferably molecules and/or proteins. Preferably, said molecules/proteins are from animal and/or human body. Alternatively, said molecules/proteins are from foods. Indeed, for example, in food industry, some treatments, preferably thermal treatments, such as milk UHT treatment, cause the glycation of food proteins and therefore the loss of organoleptic and quality profile of food. In this context, the thermostable Amadoriase protein variants of the invention can be used to avoid and/or to reduce the glycation of food proteins caused preferably by thermal treatments and/or consequently they can be used to avoid and/or to reduce the loss of organoleptic and/or the quality profile of food.

Moreover, the thermostable Amadoriase protein variants disclosed above are useful for medical purposes and/or for diagnostic purposes. Preferably, the thermostable Amadoriase protein variants disclosed above are used as biosensor, preferably to detect glycated hemoglobin. Therefore they can be used to monitor diabetes, preferably diabetes mellitus.

Indeed, the measurement of systemic heamoglobin glycation (HbA1c) is a well-established method to diagnose the insurgence and/or the development of diabetes.

Therefore, a further aspect of the present invention refers to the thermostable Amadoriase protein variants as disclosed above as diagnostic tool.

Alternatively, the thermostable Amadoriase protein variants as disclosed above can be used as therapeutic tool, preferably to reduce the in vivo glycation of molecules and/or proteins.

A further aspect of the present invention refers to a kit for measuring glycated haemoglobin and, more preferably, for evaluating/measuring diabetes, preferably diabetes mellitus. The kit is an Amadoriase-based kit that uses the thermostable Amadoriase protein variants disclosed above because these variants show an improved resistance to thermal treatment and/or to proteases.

A further aspect of the present invention refers to a method for measuring glycated haemoglobin in a biological sample, preferably in blood, said method comprising the following steps:

(i) digesting a sample comprising heamoglobin to proteases in order to release amino acids, preferably the glycated valine from the N-terminus of haemoglobin;

(ii) deglycating the valine released according to step (i) by adding the thermostable Amadoriase protein variants disclosed above;

(iii) measuring/determining the amount of hydrogen peroxide produced after step (ii).

As mentioned before, the method for measuring glycated haemoglobin in a biologic sample can be useful for determining the insurgence and/or the development of diabetes, preferably diabetes mellitus.

Example

Protein Expression and Purification

The wild type Amadoriase I gene (SEQ ID NO: 3), has been cloned in a bacterial expression vector with a cloning site (Novagen).

The double-cysteine mutations were introduced in the wild type sequence using the mutagenesis kit (Agilent).

All constructs and mutations were verified by DNA sequencing.

*E. coli* BL21(DE3)pLysS cells (Invitrogen) were then transformed with the mutated DNA and grown in Lysogeny Broth (LB) medium supplemented with 50 mg/liter ampicillin (Sigma).

Cells were grown at 37° C. until A600=0.6 was reached and expression was induced by adding isopropyl 1-thio-β-D-galactopyranoside (Sigma) to a final concentration of 0.5 mM. Subsequent overnight protein expression at 25° C. provided soluble protein. The cell lysate was then purified by nickel affinity chromatography.

A second and final purification step using a Hiprep 26/60 Sephacryl S-100 size exclusion column (GE Healthcare) was performed to provide 100% sample purity as detected by Coomassie staining. Absorbance at 450 nm was monitored in order to identify the fractions with the most intense yellow color, which is typical of FAD-dependent enzymes.

The fractions of this last affinity chromatography step were collected and dialyzed into a 10 mM Tris buffer, pH 8.0.

Different aliquots of highly purified SS-enzymes (the Amadoriase protein variants) at different concentration have been prepared and stored at −80° C. All the protein concentrations were determined using a Bradford assay14 kit (Bio-Rad) and bovine serum albumin (Sigma) as the standard.

Enzyme Activity Assay

Enzymatic activity was followed by a continuous assay that detects glucosone formation over time from fructosyl-lysine at 322 nm. The 200 µl reaction mixture contained 10 mM Tris HCl pH 7.4, 20 mM o-Phenylenediamine, 2 mM fructosyl-lysine. After 1 minute of pre-incubation, the reaction was started adding 4.5 µg of enzyme, and the increase in absorbance at 322 nm (glucosone $\varepsilon_{322}$=149.25 $M^{-1}cm^{-1}$) was monitored in a Spark10M (Tecan).

Steady-State Kinetics

Apparent steady-state parameters for the enzymes over its natural substrate were determined by means of the assay described above, with fructosyl-lysine concentrations varied from 0.05 mM to 2 mM. Data points were obtained from three independent experiments. Kinetic parameters were calculated using a non-linear least-square fit of the data, and fitted with Eq. 1 (the Michaelis-Menten equation for hyperbolic substrate kinetics) using Hyperbola fit function of GraphPad Prism version 5.00 for Windows, GraphPad Software, La Jolla Calif. USA.

$$v = \frac{V_{max} * S}{(K_m + S)} \quad \text{(Eq.1)}$$

in which v, $V_{max}$, S, and $K_m$ represent the steady state reaction rate, maximum reaction rate, substrate concentration, and Michaelis-Menten constant for the substrate, respectively.

Results of Steady-State Kinetics

Kinetics parameters calculated for the wild type and the two mutants towards fructosyl-lysine are consistent with those reported in literature for other enzymes of the same family. In particular, it is shown that for the SS03 and SS17 variants the mutations do not significantly affect the kinetic parameters when compared with the WT. In other words, the data confirmed that the introduced modifications increase the stability without impairing the catalytic properties of the enzymes.

All the kinetic data are summarized in Table II.

TABLE II

| Enzyme | $K_m$ [mM] | $k_{cat}$ [$s^{-1}$] | $k_{cat}/K_m$ [$s^{-1}$ $mM^{-1}$] |
|---|---|---|---|
| WT | 0.51 ± 0.19 | 21.55 ± 3.08 | 41.68 ± 16.48 |
| SS03 | 0.34 ± 0.13 | 21.90 ± 2.73 | 64.17 ± 25.5 |
| SS17 | 0.68 ± 0.18 | 22.91 ± 2.12 | 33.34 ± 10.16 |

Measurement of Thermal Stability

Thermal stability test was performed using the assay described above after heat treatment, by incubating for 10 minutes the enzyme to target temperature ranging from 25° C. to 100° C. (with 5° C. steps) in the absence of ligands, and then cooling it down at 4° C. until test. The reduced forms of the enzymes were obtained by supplementing the buffer with 100 mM 1,4-Dithiothreitol (DTT). After 1 h of incubation, the heat treatment and enzymatic assay are performed as for the oxidized forms. Data points were obtained from three independent experiments.

$T_{50}$ values were obtained by fitting data with Boltzmann Equation (Eq. 2) with the Boltzmann sigmoidal fit function implemented in GraphPad Prism version 5.00 for Windows, GraphPad Software, La Jolla Calif. USA.

$$A = A_{bottom} + \frac{(A_{top} - A_{bottom})}{1 + e^{\left(\frac{T-T_{50}}{S}\right)}} \quad \text{(Eq. 2)}$$

where A represents the residual activity, $A_{bottom}$ the lower asymptote of residual activity, $A_{top}$ the higher asymptote of residual activity, T the temperature, $T_{50}$ the temperature at which residual activity is halfway between $A_{top}$ and $A_{bottom}$, and s describes the steepness of the curve.

Thermal Stability Results

The thermal stability is assessed by testing the activity of Amadoriase variants from 25° C. to 100° C. and then calculating the $T_{50}$, that is the temperature at which the enzymes lose 50% of the activity with respect to the activity at 25° C. (see FIG. 2 and Table III).

TABLE III

| Enzyme | $T_{50}$ [° C.] | $\Delta T_{50}$ [° C.] |
|---|---|---|
| WT | 52.40 ± 0.69 | — |
| SS03 | 55.25 ± 3.28 | +2.85 |
| SS17 | 60.62 ± 0.95 | +8.22 |

The results show that the Amadoriase variants of the invention—SS03 and SS17—display a significant improvement in $T_{50}$ compared to the wild type (WT) enzyme, of ≈3° C. and ≈8° C., respectively.

It is worth noting that, while wild type and SS03 lose completely their activity at temperatures 60° C., the SS17 mutant retains a residual activity of 50% at 60° C. and it is still active after heat treatment at 90° C. (with 6% residual activity (see FIG. 2).

To confirm the disulfides bonds formation we performed the same experiments supplementing the buffer with 100 mM Dithiothreitol (DTT), in order to reduce the disulfide bonds.

The results show that all the SS-variants lose the improved thermal resistance and behave very similar to the wild type.

Protein Crystallization and Structure Determination

Crystals of both the SS03 and the SS17 mutant were obtained using the vapor diffusion method at room temperature by mixing a 1 μl drop of ~15 mg/ml protein sample with an equal volume of a 0.1 M sodium citrate pH 5.6, 14% PEG4K, 15 isopropanol and 0.1 M sodium citrate pH 5.6, 14% Peg4K, 5% dimethyl sulfoxide solution respectively. Medium-size (150×100×50 μm) rod-like crystals appeared within a few days. Prior to X-ray data collection, crystals were frozen in a chemically identical solution supplemented with 25% (v/v) glycerol for cryo-protection. A 2.19 Å resolution data set was collected from a crystal of SS03 and a 2.85 Å resolution data set was collected from a crystal of SS07, in both cases using λ=1.000 Å in the X06DA-PXIII beamline at the Swiss Light Source (Paul Scherrer Institute, Villigen, Switzerland). Diffraction images were processed and scaled using XDS. The structures were determined by molecular replacement using MOLREP from the CCP4 package and the free Amadoriase I structure (PDB code: 4WCT) as the search probe. Model building and refinement were carried out using REFMAC5 and PHENIX. Water molecules were added both automatically using the phenix_refine tool from the PHENIX package and manually from visual inspection of the electron density map.

The invention claimed is:

1. An isolated thermostable Amadoriase protein characterized by the replacement of amino acid serine in position 67 (S67) and/or proline in position 121 (P121) and/or aspartic acid in position 295 (D295) and/or lysine in position 303 (K303) with cysteine (C), wherein the amino acid position refers to the amino acid sequence of the wild type Amadoriase, that has amino acid sequence SEQ ID NO: 1, or a polynucleotide sequence codifying said isolated thermostable Amadoriase, wherein said polynucleotide sequence is SEQ ID NO: 5 or 7, or a recombinant vector comprising the polynucleotide, or a host cell comprising the polynucleotide or the recombinant vector or permanently expressing the thermostable Amadoriase protein.

2. The isolated thermostable Amadoriase protein according to claim 1, wherein the mRNA/cDNA corresponding to SEQ ID NO: 1 is SEQ ID NO: 2 and/or SEQ ID NO: 3.

3. The isolated thermostable Amadoriase protein according to claim 1 characterized by an amino acid sequence comprising SEQ ID NO: 4 and/or 6.

4. The isolated thermostable Amadoriase protein according to claim 1 conjugated and/or flagged and/or marked, at the C-end and/or at the N-end, with metals, fluorophores, dyes, tags and reporters.

5. The isolated thermostable Amadoriase protein according to claim 4, wherein the tag is selected from: a histidine tag, a GST tag and a MBP tag.

6. A method for reducing the glycation of molecules or proteins derived from animal or human body or from foods, said method comprising
   contacting said molecules or proteins with the isolated thermostable Amadoriase protein according to claim 1.

7. The method according to claim 6, wherein said food is subjected to a thermal treatment.

8. An in vivo method for reducing glycation of molecules or proteins said method comprising
   administering to an individual in need thereof an effective amount of the isolated thermostable Amadoriase protein, or the polynucleotide sequence according to claim 1.

9. A method for measuring glycated haemoglobin in a biologic sample or for determining the insurgence or the development of diabetes said method comprising the following steps:
- (i) digesting a sample comprising haemoglobin with proteases in order to release amino acids;
- (ii) deglycating the amino acids released according to step (i) by adding the thermostable Amadoriase protein according to claim 1; and
- (iii) measuring/determining the amount of hydrogen peroxide produced after step (ii).

* * * * *